(12) United States Patent
Thorens et al.

(10) Patent No.: US 10,342,260 B2
(45) Date of Patent: Jul. 9, 2019

(54) AEROSOL-GENERATING DEVICE INCLUDING REVERSIBLY CONNECTED HEATER AND RELEASE MEDIUM

(71) Applicant: Philip Morris Products S.A., Neuchatel (CH)

(72) Inventors: Michel Thorens, Moudon (CH); Ihar Nikolaevich Zinovik, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 52 days.

(21) Appl. No.: 15/535,467

(22) PCT Filed: Dec. 15, 2015

(86) PCT No.: PCT/EP2015/079881
§ 371 (c)(1),
(2) Date: Jun. 13, 2017

(87) PCT Pub. No.: WO2016/096912
PCT Pub. Date: Jun. 23, 2016

(65) Prior Publication Data
US 2017/0367409 A1    Dec. 28, 2017

(30) Foreign Application Priority Data
Dec. 15, 2014   (EP) .................................... 14198014

(51) Int. Cl.
*A24F 13/00*    (2006.01)
*A24F 17/00*    (2006.01)
(Continued)

(52) U.S. Cl.
CPC ........... *A24F 47/008* (2013.01); *A61M 15/06* (2013.01); *A61M 11/044* (2014.02); *A61M 15/0068* (2014.02)

(58) Field of Classification Search
CPC ... A24F 47/008; A24F 47/002; A61M 11/042; H05B 3/06
(Continued)

(56) References Cited

U.S. PATENT DOCUMENTS 5,591,368 A * 1/1997 Fleischhauer ......... A24F 47/008
131/194
9,326,547 B2 * 5/2016 Tucker ................. A24F 47/008
(Continued)

FOREIGN PATENT DOCUMENTS

EP    2 340 729 A1    7/2011

OTHER PUBLICATIONS

International Search Report and Written Opinion dated Apr. 20, 2016 in PCT/EP2015/079881, filed Dec. 15, 2015.

*Primary Examiner* — Abdullah A Riyami
*Assistant Examiner* — Thang H Nguyen
(74) *Attorney, Agent, or Firm* — Oblon, McClelland, Maier & Neustadt, L.L.P.

(57) ABSTRACT

An aerosol-generating device is provided, including a reservoir configured to hold a liquid; a release medium; and a heater, wherein the reservoir and the release medium are configured to transport liquid from the reservoir to the release medium, wherein the release medium and the heater are disposed in physical contact with each other, wherein the aerosol-generating device further includes a means for reversibly releasing the physical contact between the release medium and the heater to form a gap between the heater and the release medium, and wherein the aerosol-generating device is configured to activate the heater when the gap is formed between the heater and the release medium. A method for forming an aerosol by the aerosol-generating device is also provided.

17 Claims, 4 Drawing Sheets

(51) Int. Cl.
    *A24F 25/00*      (2006.01)
    *A24F 11/00*      (2006.01)
    *A24F 47/00*      (2006.01)
    *A61M 15/06*      (2006.01)
    *A61M 11/04*      (2006.01)
    *A61M 15/00*      (2006.01)

(58) Field of Classification Search
    USPC .................................................. 131/329, 328
    See application file for complete search history.

(56) References Cited

U.S. PATENT DOCUMENTS

| | | | |
|---|---|---|---|
| 9,986,761 B2* | 6/2018 | Thorens | A24F 47/008 |
| 2011/0155153 A1 | 6/2011 | Thorens et al. | |
| 2013/0192615 A1 | 8/2013 | Tucker et al. | |
| 2013/0192616 A1 | 8/2013 | Tucker et al. | |
| 2013/0192619 A1 | 8/2013 | Tucker et al. | |
| 2013/0192620 A1 | 8/2013 | Tucker et al. | |
| 2013/0192621 A1 | 8/2013 | Li et al. | |
| 2013/0192622 A1 | 8/2013 | Tucker et al. | |
| 2013/0192623 A1 | 8/2013 | Tucker et al. | |
| 2014/0069424 A1* | 3/2014 | Poston | A24F 47/008 |
| | | | 128/202.21 |
| 2015/0264979 A1 | 9/2015 | Thorens et al. | |
| 2017/0333650 A1* | 11/2017 | Buchberger | A61M 15/06 |

* cited by examiner

AEROSOL-GENERATING DEVICE INCLUDING REVERSIBLY CONNECTED HEATER AND RELEASE MEDIUM

TECHNICAL FIELD

The present invention relates to an aerosol-generating device which comprises a reservoir for a liquid, a release medium and a heater and to an aerosol-generating system containing this aerosol-generating device.

DESCRIPTION OF THE RELATED ART

It is known to use aerosol-generating devices in aerosol-generating systems such as electrical aerosol-generating systems. For example, EP 2 493 341 B1 describes such a device in which liquid from a storage container is transported to a capillary wick which is at least partially surrounded by a coil of wire where the coil of wire is in physical contact with the capillary wick. The coil of wire is connected to a battery. If electric current is applied to the wire, it will heat up and will volatize the liquid on the wire. The volatized liquid is taken up by an air flow which passes from an air inlet via the capillary wick and its surrounding wire to an air outlet. The volatized liquid in the airflow or air stream will condense into an aerosol which will then be inhaled by the consumer.

A disadvantage of such existing systems is that the dose of the vaporized and later aerosolized liquid is difficult to be controlled. For the above-described coil and capillary wick heater according to EP 2 493 341 B1 the amount of liquid on the heater but in addition also some of the liquid in the capillary wick immediately adjacent to the heated wire will be vaporized. Depending on the duration of the heating action, which normally corresponds to the duration of the consumer's puff, also some of the liquid might undergo a vaporization which is replenished during the puff by the capillary forces in the capillary wick for the already vaporized material. For these reasons it is difficult to exactly define and control the dose of liquid which is vaporized during a single puff by the consumer.

It would, however, be desirable to be able to provide the consumer with a smoking system for which the dose of liquid vaporized during each puff can be more accurately controlled.

SUMMARY

This problem can be alleviated by using an aerosol-generating device comprising a reservoir with a liquid, a release medium, and a heater, wherein the reservoir and the release medium are in contact with each other such that during use of the aerosol-generating device liquid is transported from the reservoir to the release medium, and wherein the release medium and the heater are arranged such that the heater and the release medium are in contact with each other such that during use of the aerosol-generating device liquid on the heater is heated. As a consequence of the heating the liquid on the heater is vaporized and then forms an aerosol. The aerosol-generating device further comprises a means for reversibly and at least partially releasing physical contact between release medium and heater such that reversibly and at least partially the contact between heater and release medium is interrupted and a gap between heater and release medium is formed. That means that during heating of the heater and vaporization of the liquid on the heater the contact between heater and release medium can be at least partially and preferably completely interrupted. As a consequence thereof, preferably only the amount of liquid which is on the heater before heating will be vaporized during heating, preferably meaning that only a defined amount of liquid will be vaporized. This may be also partially possible if there remains a partial contact between heater and release medium during heating since then depending on the extent of contact and the duration of heating in addition to the liquid on the heater a rather precisely defined additional amount of liquid will be transferred during the heating step from the release medium to the heater and then be vaporized. However, in order to be able to most precisely define the amount of liquid to be vaporized it is preferred that there is no contact between heater and release medium during heating.

BRIEF DESCRIPTION OF THE DRAWINGS

Embodiments of the invention will now be further described, by way of example only, with reference to the accompanying drawings in which.

DETAILED DESCRIPTION

Figure 1:
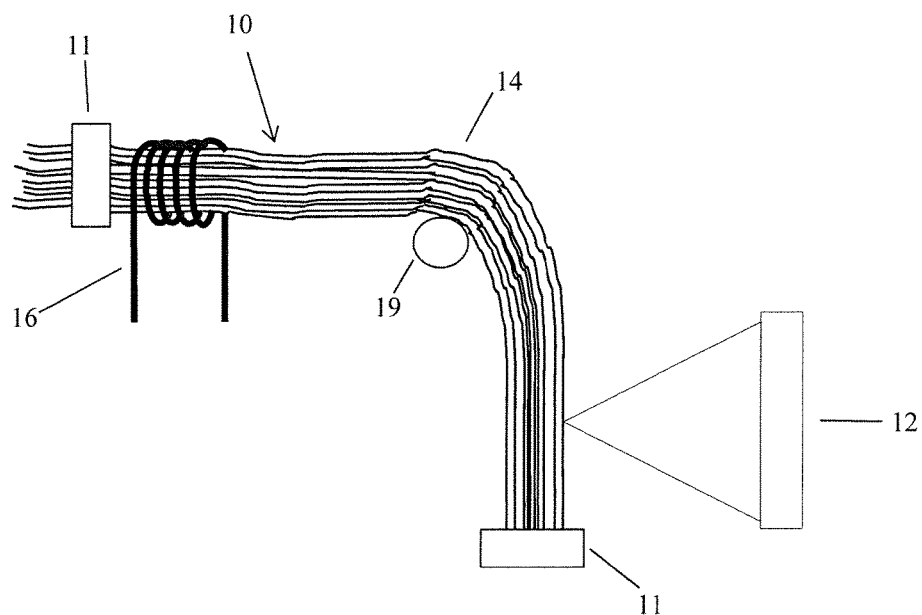
FIG. 1 shows an example of the third embodiment before stretching of the wick.

An aspect of the invention provides an aerosol-generating device comprising a reservoir for containing a liquid, a release medium, and a heater, wherein the reservoir is arranged to deliver liquid from the reservoir to the release medium, wherein the device includes a mechanism for moving the release medium, the heater, or both between a first configuration in which the release medium and the heater are in contact with each other and a second configuration in which there is a gap between the heater and the release medium, wherein the device is adapted to turn on the heater while the heater and release medium are in the second configuration, and turn off the heater when the release medium and the heater are in the first configuration.

A further aspect of the invention provides an aerosol-generating device comprising a reservoir for a liquid, a release medium, and a heater, wherein the reservoir and the release medium are arranged, during use of the aerosol-generating device liquid to transport liquid from the reservoir to the release medium, wherein the release medium and the heater are arranged such that the heater and the release medium are in physical contact with each other, and wherein the aerosol-generating device further comprises a means for reversibly releasing the physical contact between release medium and heater such that a gap between heater and release medium is formed, wherein the device is adapted to activate the heater when the gap is formed between the heater and the release medium.

The aerosol-generating device according to the subject invention allows a more accurate control of the amount of liquid released in a single puff. Because the heater is at least partially removed from the liquid-containing release medium such that no longer any physical contact or at least a limited physical contact remains and a gap is formed between these two elements, the amount of liquid will be limited and controlled and only the liquid which is on the heater, in particular on the surface of the heater, will be vaporized. Because of the gap between heater and release medium vaporization will not occur of any liquid in the previous contact area and in neighboring regions of the release medium. Also any liquid which is transported from the reservoir to the release medium to replace the liquid being transported to the heater will not be vaporized during warming up of the distant heater.

The invention also relates to an aerosol-generating system comprising one of the aerosol-generating devices according to the subject invention, an energy source which is connected to the heater and either to a releasing means or to an air flow sensor, and at least one air inlet and at least one air outlet which are arranged so as to define an air flow route from the at least one air inlet via the heater to the at least one air outlet so as to convey the vapour formed at the heater and the aerosol resulting therefrom to the at least one air outlet. More preferably the aerosol-generating system of the subject invention further comprises a housing which includes the at least one air inlet and at least one air outlet and houses the remaining components of the aerosol-generating device.

An aspect of the present invention further provides a method for heating liquid in an aerosol-generating device comprising a reservoir containing a liquid, a release medium, and a heater, wherein the reservoir is arranged to deliver liquid from the reservoir to the release medium, the method comprising the steps of arranging the release medium and the heater in a first configuration in contact with each other such that liquid is transported from the release medium to the heater, and moving the release medium, the heater or both to a second configuration in which there is a gap between the heater and the release medium, and returning the release medium and heater to the first configuration, wherein the method further includes the step of heating the heater while the heater and release medium are in the second configuration. Preferably the method further includes the step of turning off the heater when the release medium and the heater are in the first configuration.

The invention further relates to a method for forming an aerosol in an aerosol-generating device comprising a reservoir with a liquid, a release medium, and a heater, wherein the reservoir and the release medium are in contact with each other such that during use of the aerosol-generating device liquid is transported from the reservoir to the release medium, and wherein the release medium and the heater are arranged such that the heater and the release medium are in contact with each other at one point of time but not permanently during use of the aerosol-generating device such that during contact of the release medium and the heater liquid is transported from the release medium to the heater, the method comprising reversibly releasing physical contact between release medium and heater such that reversibly the contact between heater and release medium is interrupted and a gap between heater and release medium is formed, and heating the heater when the physical contact between release medium and heater is interrupted and a gap between heater and release medium is formed, such that liquid on the heater is heated and forms an aerosol.

The liquid used in the aerosol-generating device and the aerosol-generating system according to the subject invention can be any liquid which is a liquid at 23 degree Celsius and can be vaporized at the temperatures provided by the heater, such as temperatures in the range of from 100 degree Celsius to 300 degree Celsius, preferably from 150 degree Celsius to 300 degree Celsius, and more preferably from 200 degree Celsius to 300 degree Celsius. Preferably the liquid contains a tobacco-originating material such as volatile tobacco flavour compounds which are released from the liquid upon heating. It is preferred that the liquid contains non-tobacco-originating materials, such as natural or artificial flavours. The liquid preferably comprises from 0.1% to 5%, for example from 0.2% to 3% by weight of flavours. It is more preferred that the liquid contains nicotine, preferably from 0.1 to 10%, for example from 0.5% to 2% by weight of nicotine. It is further preferred that the liquid contains an aerosol former, such as glycerine or propylene glycol or mixtures thereof. The liquid may comprise from 50% to 95%, more preferably from 70% to 85% by weight of an aerosol former such as glycerine or propylene glycol or mixtures thereof. Preferably the liquid contains water, more preferably from 5% to 30% or from 10% to 20% by weight of water.

The aerosol-generating device according to the subject invention is adjusted such that the amount of liquid which is vaporized during each puff is preferably 1 to 4 mg of liquid, more preferably 2 to 3 mg of liquid. That means, that the release medium, its contact to the reservoir, its capillarity and its dimensions, the heater and the contact area between heater and release medium are adjusted such that preferably 1 to 4 mg of liquid, more preferably 2 to 3 mg of liquid are transferred for each puff of the consumer from the release medium to the heater and then vaporized during the time period the heater is activated.

The amount of liquid which is vaporized during each puff can be determined by measuring the weight of the aerosol-generating device before and after a puff. The weight difference is the amount of liquid which has been vaporized during the puff.

The means for reversibly and at least partially releasing physical contact between release medium and heater can either be activated and deactivated automatically during use of the aerosol generating device or alternatively be switched on and off by a releasing means.

The automatic activation and deactivation of the means for reversibly and at least partially releasing physical contact between release medium and heater may be achieved by an air flow sensor. The automatic activation and deactivation of the heater may be achieved by an air flow sensor, too. Thus, if the consumer draws on the aerosol-generating system of the subject invention, this will cause an air flow. The air flow in turn will move, e.g., a valve or blade, or activate an air flow sensor. This movement of the valve or blade or the activation of the air flow sensor will lead to a contact or a closing of a circuit which then activates the heater or means for reversibly and at least partially releasing physical contact between release medium and heater or both. Once the puff of the consumer is terminated the air flow will stop so that the valve or blade will return to its original position and the previous contact is lost. As a consequence, the heater or the means for reversibly and at least partially releasing physical contact between release medium and heater or both will automatically be deactivated.

The means for reversibly and at least partially releasing physical contact between release medium and heater is a device arranged to release physical contact between release medium and heater.

The realising means for switching on and off the means for reversibly and at least partially releasing physical contact between release medium and heater is preferably a button, a slide switch or a rotary switch, more preferably a button. The realising means can also be an electronical device which issues a signal or a pulse which in turn will switch on and off the means for reversibly and at least partially releasing physical contact between release medium and heater.

According to a first embodiment of the subject invention, the heater is also the means for reversibly and at least partially releasing physical contact between release medium and heater and may be a mesh heater disk which comprises at least two different materials which upon heating lead to different deformations. Such a mesh heater disk can be a warp and weft net made of two or more, more preferably two, different materials which have different thermal deformation properties. Potential materials for such a mesh heater disk are metal fibres made of stainless steel fibers, for example made of stainless steel alloys of series 300 and 400, or NiCr alloys (nickel chromium alloys) with a fiber diameter of 9 to 50 micrometers or non-metallic fibers such as carbon fibers with high content of pure carbon or mixtures thereof. The release medium can be made of fibrous mats of polypropylene, polyethylene, polyethylene terephthalate, polybutylene terephthalate, or their composites with pore sizes from 0.4 micrometers to 15 micrometers or polymer fibres made from a polymer with sufficient thermal stability to sustain temperatures occurring during use of the aerosol-generating device such as 100-300 degree Celsius. The fibres for making the mesh heater disk are fixed to each other at the outer ends of the mesh heater disk. In the unheated condition the mesh heater disc is a flat disc or a flat sheet of preferably round or rectangular, more preferably round shape. It will lie on the release medium. The release medium for the first embodiment can be a disc made of the fibrous mats of materials as described above. More preferably the shapes and sizes of the release medium and of the mesh heater disc are identical. Since release medium and mesh heater disc will lie on each other and have more preferably same sizes and shapes, they are in the unheated condition in close physical contact, meaning that liquid can be transported from the release medium to the mesh heater disc until an equilibrium is established. The release medium of the first embodiment is either directly or indirectly via an intermediate diffusion media connected to the reservoir for the liquid. The reservoir is more preferably a container which contains the liquid. For example, the release medium of the first embodiment can be a spongy or fibrous wick material such as those described above, namely fibrous mats of polypropylene, polyethylene, polyethylene terephthalate, polybutylene terephthalate, or their composites with pore sizes from 0.4 micrometers to 15 micrometers, which extends into or is in contact with the liquid-containing container. The spongy or fibrous nature of the wick material will have the effect that any liquid which was removed from the release medium and has been transported to the heater will be replenished automatically and will be transported by capillary forces from the container to the release medium.

When the mesh heater disk of the first embodiment contains at least two different materials with different thermal deformation properties the mesh will upon heating undergo a deformation. One of the materials of the mesh heater disk will for example not change its form upon heating whereas the other might expand. Since the fibres for making the mesh heater disk are fixed to each other at the outer ends of the mesh heater disk, this expansion will lead to the disk being bent when heated. As a consequence the mesh heater disk lying without heating in flat contact with the release medium will upon heating and bending loose contact with the release medium at least at its centre region. Only the outer edges of the mesh heater disk where the fibres of different materials are connected to each other will stay in touch with the release medium. Thus, a more or less complete interruption of the contact of the release medium and the mesh heater disk is achieved by heating.

This heating can be initiated by switching on a releasing means. The releasing means will close an electric circuit between the mesh heater disk and the energy source such as a battery. The electric current will cause the metallic fibers in the mesh heater disk to heat up. For example, the consumer when drawing on the aerosol-generating system can press a button which will close the mentioned electric circuit and will lead to heating of the mesh heater disk. As a result of the heating, the liquid on the mesh heater disk will vaporise and form an aerosol which can be inhaled by the consumer. However, since the contact between mesh heater disc and release medium will be lost nearly completely when the mesh heater disk is heated and deforms, the amount of liquid vaporised is limited to the amount of liquid on the heater at the beginning of the heating action. Once the consumer no longer continuous to press to button, the electric circuit will be interrupted, the mesh heater disk will cool down and will return to its original position and will get in contact again with the release medium. Liquid will be transferred from the release medium to the mesh heater disk (and, of course, as a consequence from the container to the release medium) which then can be vaporised during the next puff.

Heating of the mesh heater disk may be initiated automatically. As described above, the drawing of the consumer on the aerosol-generating system can initiate the movement of a blade or a valve. This will automatically close an electric circuit and initiate an electric current which will lead to heating of the mesh heater disk in the same way as described above. Once the consumer stops drawing on the aerosol-generating system, the valve or blade will return in its original position and the electric circuit will be interrupted, the mesh heater disk will cool down and vaporization will automatically be terminated.

According to a second embodiment of the subject invention the heater is also the means for reversibly and at least partially releasing physical contact between release medium and heater and may be a mesh heater disk with a ring surrounding closely the mesh heater disk. The mesh heater disk and the surrounding ring may be made from different materials, and the surrounding ring may be deformable upon heating. The electric circuit described above for the first embodiment may incorporate for the second embodiment the mesh heater disk and the surrounding ring. Thus, there is an electrical contact between mesh heater disk, surrounding ring and energy source. If this electric circuit is closed, this will lead to heating of the surrounding ring and optionally, if metallic fibers are included within the mesh heater disk, also of the same. Thus, for this second embodiment the surrounding ring and the mesh heater disk are preferably made of two different materials with different thermal deformations. For example, the mesh heater disk can again be made as a warp and weft net as described above from metallic fibres such as stainless steel fibers, for example made of stainless steel alloys of series 300 and 400, or NiCr alloys with fiber diameter from 9 micrometers to 50 micrometers or non-metallic fibres such as carbon fibers with high content of pure carbon or mixtures thereof. The release medium can again be made of fibrous mats of polypropylene, polyethylene, polyethylene terephthalate, polybutylene terephthalate, or their composites with pore size from 0.4 micrometers to 15 micrometers. The ring surrounding the mesh heater disk can be made of materials such as bimetal actuators (snap action) as well as piezoelectric displacement actuators that may be clamping sections around the mesh heater disk. The piezo actuator may be a small tube actuator with vertical or lateral displacement driven by the air flow sensor or the manual switch to stretch or squeeze the ring surrounding the mesh heater disk.

As for the first embodiment heating of the surrounding ring and optionally the mesh heater disk can be initiated by the consumer by switching on a releasing means such as button and terminated by switching off the releasing means such as a button. Alternatively, again the heating can be activated automatically by way of the above-described air flow sensor or puff sensor which leads during a puff to closing of an electric circuit which heats up the deformable ring and optionally the mesh heater disk. The surrounding ring must be in close contact and in the immediate vicinity of the mesh heater disk with the consequence that the deformation upon heating of the ring surrounding the mesh heater disk can and will lead to deformation of the mesh heater disk. As a consequence the mesh heater disk is bent away from the release medium so that the contact between mesh heater disk and release medium is more or less completely interrupted and a gap between these two elements is formed. This will again have the effect that during a puff and during heating of the surrounding ring and optionally the mesh heater disk only the liquid which is on the mesh heater disk can be vaporized, meaning that control of the amount of liquid to be vaporized is possible.

According to a third and more preferred embodiment of the subject invention the release medium is a capillary wick and the heater is a coil of wire which at least partially surrounds the capillary wick.

The capillary wick may have a fibrous structure. The fibrous wick materials can be made of ceramic, graphite or fiberglass materials in the form of fibers having preferably a diameter of 5 to 20 micrometer. Preferably, the capillary wick comprises a plurality of fibres or threads. More preferably these fibres or threads are not completely stretched but are in a relaxed state and have a somehow wavelike or crimped structure which allows stretching. The more preferred plurality of fibres forms a capillary wick or a kind of a yarn. It is similarly more preferred that the wick has an elongated or rod-like structure. As mentioned, one part of the capillary wick is surrounded by a coiled wire. A second part of the capillary wick extends into or is in contact with the reservoir for the liquid which is again more preferably a container. The empty space between the single fibres of the capillary wick allows transport of the liquid by capillary forces. That means, if at one part of the capillary wick some of the liquid is removed, by direct vaporization or indirectly by transfer to the coil of wire wherefrom vaporization occurs, the capillary nature of the capillary wick will automatically take care that liquid is replenished from the reservoir into the area where liquid has been removed by vaporization. As the capillary wick more preferably extends into the reservoir with the liquid, constant equilibrium is always given: a defined amount of liquid is removed by vaporization and the capillary forces supply replacement liquid from the reservoir through the capillary wick into the area where vaporization has occurred.

At least part of the capillary wick is surrounded by a coil of wire such that the wire is in contact with the wick in the initial state. Typically the wire is provides with 4 to 8 turns around the wick. Materials for the wire are metals such as nickel chromium alloys or stainless steel alloys for examples of series 300 and 400.

If electric current is applied, as will be described below, to the coiled wire it will heat up and lead to a vaporization of the liquid which has been transferred from the capillary wick to the coiled wire. In order to interrupt the intimate contact between capillary wick and wire the capillary wick can be stretched. Stretching can be achieved more preferably by a button. If the consumer presses the button, this will have two separate effects. The first effect is that by pressing the button an electric circle is closed so that the wire is heated up and vaporizes the liquid on the wire. At the same time the button will interact with the capillary wick and will stretch it such that its length is increased and at the same time its diameter is decreased. Stretching can be achieved by fixing the wick at its ends and providing the button with an elongation with is in contact with the wick. If the consumer presses the button, this movement will be continued by the button's elongation which will stretch the flexible wick. Decreasing of the diameter will in turn have the effect that the contact between capillary wick and the coiled wire is completely interrupted and a gap results between capillary wick and coiled wire. Thus, only the amount of liquid which is on the coiled wire when the consumer presses the button can be vaporized and then later on inhaled by the consumer in the form of an aerosol. Once the consumer stops pressing the button, the electric circuit will be interrupted, the stretching of the capillary wick will be discontinued meaning that the capillary wick will get again in contact with the now cooling or already cold coiled wire. Liquid can again be transferred from the capillary wick to the coiled wire and upon activation of the heating step by pressing the button again a second puff can be made by the consumer.

A preferred alternative for stretching the wick is by providing the button to be pressed by the consumer with an elongation, where the elongation of the button is connected to one end of the wick. The other end of the wick is fixed. Pressing of the button by the consumer is translated into a rotation along an axis perpendicular to the longitudinal axis of the wick, and at the same time closes an electric circuit leading to heating of the coiled wire. As a consequence, part of the wick is wound around the elongation. This winding of the wick results in a decrease of the wick's diameter, meaning that the contact between wick and coiled wire will be lost and a gap results. If the consumer releases the button, the wick is unwound from the button's elongation, the diameter is increased, the wick will get in contact again with the coiled wire and the electric circuit will at the same time be interrupted.

A further preferred alternative to stretch the wick is that the button to be pressed by the consumer is provided with an elongation which is connected to one end of the wick. The other end of the wick is fixed. If the button is pressed by the consumer, this will be translated into a rotation of the elongation and the wick's end which is fixed to this elongation around the longitudinal axis of the wick, and at the same time an electric circuit leading to heating of the coiled wire will be closed. As a consequence the wick is twisted around its longitudinal axis. This twisting of the wick leads to a reduction of the diameter meaning that the contact between wick and coiled wire is completely lost and a gap results. If the consumer releases the button the reverse rotation occurs, meaning that the wick is untwisted, the diameter is increased, the wick will get in contact again with the coiled wire and the electric circuit will at the same time be interrupted.

According to a fourth embodiment of the subject invention the heater is again a mesh heater disk as defined above for the first and second embodiments. The release medium for the fourth embodiment is as defined above for the first and second embodiment. The mesh heater disk is surrounded by a deformable ring. This surrounding and deformable ring is in close contact with the mesh heater disk. For this fourth embodiment the surrounding and deformable ring can be made of materials such as elastic metals and elastic polymers. Preferably the deformable ring is made of corrugated stainless steel foil, elastic polyamide, or piezoceramic materials, such as polycrystalline ferroelectric ceramics. Examples of such polycrystalline ferroelectric ceramics are barium titanate ($BaTiO_3$) and lead zirconate titanate.

For the fourth embodiment the heating and vaporization step is initiated by the consumer by pressing a button. This will have two separate effects. The first effect is that by pressing the button an electric circle is closed so that the mesh heater disk is heated up and vaporizes the liquid on the mesh heater disk. At the same time the button will interact with the surrounding ring and will deform it as a consequence of the physical interference of the button with the surrounding ring. The deformation of the surrounding ring will lead to a deformation of the mesh heater disk. This deformation of the mesh heater disk will have the result that the mesh heater disk is bent and will at least at its center parts lose contact between the mesh heater disk and the release medium. Thus, because of the interruption of the contact between the mesh heater disk and the release medium only the amount of liquid which is on the mesh heater disk can be vaporized. If the consumer discontinues to press the button, the electric circuit will be interrupted meaning that the mesh heater disk will cool down and at the same time the physical interaction between the button via the surrounding ring to the mesh heater disk will cease meaning that the mesh heater disk can return to its original position. Thus, the cooling or already cold mesh heater disk will get in contact again with the release medium, and liquid replenish to the release medium can be transferred by capillary forces to the mesh heater disk which upon pressing the button can undergo again the above-described steps and vaporize additional material for the consumer.

According to a fifth embodiment of the subject invention the release medium is as defined above for the first and second embodiments and the heater is a magnetically activated mesh heater disk. In addition, a magnet is provided for this fifth embodiment. Activation of this aerosol-generating device can be achieved either automatically via an air flow sensor or puff sensor as described above or by the consumer by pressing the button. In either way, activation will lead to, preferably an alternating electric current and in consequence, the magnetic field being switched on which will apply a magnetic force onto the magnetically activated mesh heater disk. Activation of the system will at the same time have the effect that an electric circuit is closed which will not only activate the magnetic field but at the same time also close an electric current which leads to heating of the magnetically activated mesh heater disk. This application of a magnetic force will lead to the magnetically activated mesh heater disk being bent or displaced at least partially away from the release medium which then has the same consequences as described above that only the amount of liquid which is on the magnetically activated mesh heater disk can be vaporized. Once the consumer either terminates the puff or discontinues to press the button the electric circuit will be interrupted meaning that the mesh heater disk will cool down. At the same time also the magnetic field will be deactivated meaning that no longer a magnetic force is applied to the magnetic mesh heater disk. This means that the cooling or already cold mesh heater disk will return to its initial form and will get in contact again within the release medium. Thus, fresh liquid can be transferred by capillary forces from the release medium to the magnetic mesh heater field.

For this fifth embodiment the magnetic mesh heater disk can be made of materials such as stainless steel fibers made of stainless steel alloys of series 300 and 400, or NiCr alloys. The magnet can be a magnet made of permanent magnetic alloys of Fe, Cr, Co, Mo, V, Al, Ni.

A preferred embodiment of the subject invention is the combination of the above-described preferred meanings. A particularly preferred embodiment of the subject invention is the combination of the above-described more preferred meanings.

FIG. 1 shows an aerosol-generating device 10 with, among others, the wick 14 which is fixed at both of its ends, for example by way of clamps 11. The wick 14 is made of a plurality of single fibers, which are in a relaxed or upstretched condition. At one of the two ends the wick 14 extends through the clamp 11 and is connected to the reservoir (such as reservoir 42 shown in FIG. 6). As a consequence, liquid from the reservoir can be transported by capillary forces from the reservoir into and through the wick 14. In addition, the coiled wire 16 surrounding and being in contact with part of the wick 14 is shown. The coiled wire 16 is in physical contact with the wick 14, meaning that liquid from the wick 14 will migrate to the wire's 16 surface. Eventually. FIG. 1 also shows the button 12 which can be pressed by the consumer. In FIG. 1, this button 12 is not yet pressed so that no stretching is applied to the wick 14.

Figure 2:
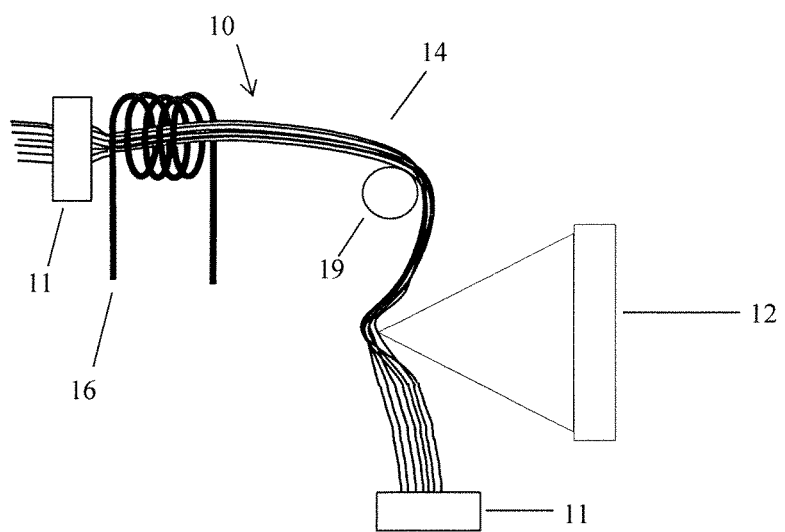
FIG. 2 shows an example of the third embodiment shown in FIG. 1 with the wick being stretched.

In FIG. 2, the same embodiment is shown as discussed for FIG. 1. The button 12 is now pushed by the consumer. The part of the button 12 which is just lying on the wick 14 according to FIG. 1 has now made a lateral movement and has increased in FIG. 2 the length of the fixed wick 14. As a result of this stretching and increasing of the length around member 19, the diameter of the wick 14 has been decreased. A comparison of FIGS. 1 and 2 shows that the wick 14 made of fibrous materials is in contact with the surrounding coiled wire 16 according to FIG. 1 but after stretching and decreasing of the diameter has lost this contact to the coiled wire 16 in FIG. 2. Parallel to stretching of the wick 14 the coiled wire 16 is connected to a power source (such as energy source 38 shown in FIG. 6), which will heat up the wire 16 and evaporate the liquid on the wire's 16 surface. Since due to the stretching wick 14 and coiled wire 16 are no longer in contact with each other, only the amount of liquid will be evaporated which is on the wire's 16 surface but none of the liquid which is in the wick 14 and in the areas of the wick 14 which are in contact with the wire 16 in the wick's 14 relaxed state according to FIG. 1. If the consumer will stop pressing the button 12, as in FIG. 2, the wick 14 will return to its original position, as it is shown in FIG. 1.

Figure 3:
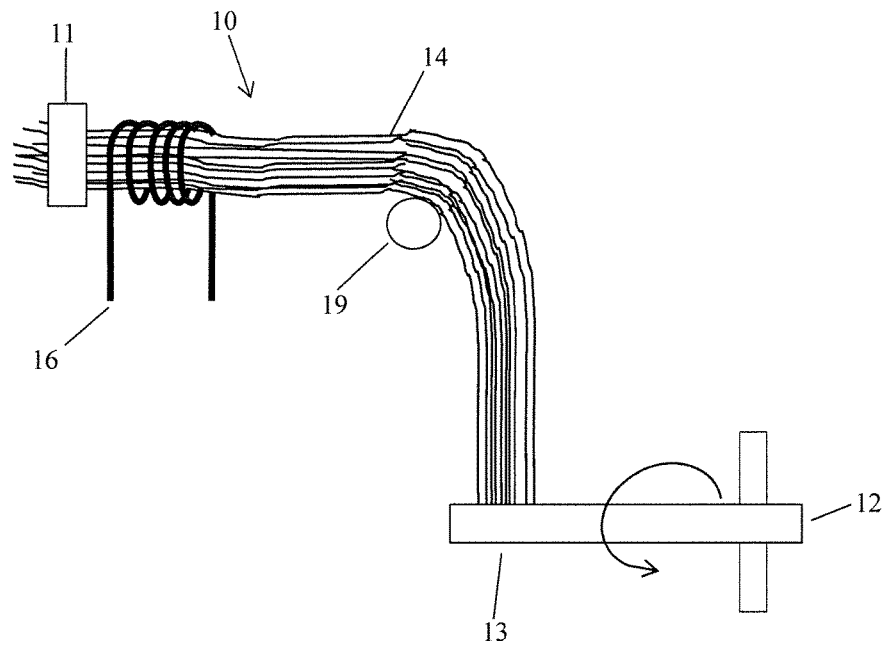
FIG. 3 shows a further example of the third embodiment before stretching the wick.
Figure 4:
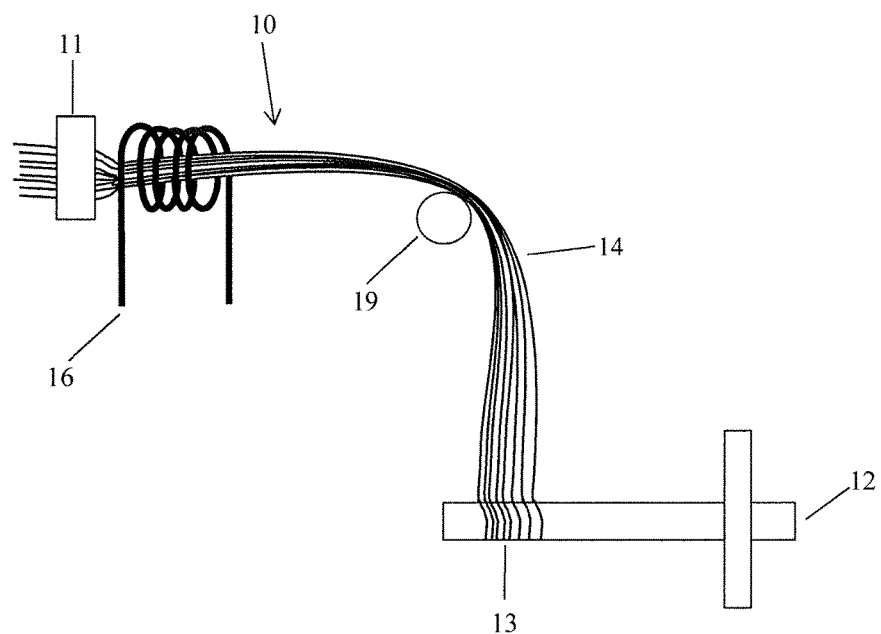
FIG. 4 shows an example of the third embodiment shown in FIG. 3 with the wick being stretched.

FIGS. 3 and 4 show a slightly different aerosol-generating device 10 and a slightly different way to stretch the wick 14 compared to FIGS. 1 and 2. In FIG. 3 again the wick 14 is in its relaxed state and in touch with the surrounding coiled wire 16. As for FIG. 1 both ends are fixed, however, in FIG. 3 one of the two ends of the wick 14 is connected to part 13 of the button 12. Pressing the button 12 by the consumer will lead to a pulling or rotation of the elongation of the button 12 along an axis perpendicular to the longitudinal axis of the wick 14. This can be seen in FIG. 4 where due to this pulling or rotation the wick 14 is rolled onto the elongation of the button 12. This leads to stretching of the wick 14 and, as a consequence, a reduction of the wick's 14 diameter and, as a further consequence, loss of contact between wick 14 and the surrounding coiled wire 16.

Figure 5:
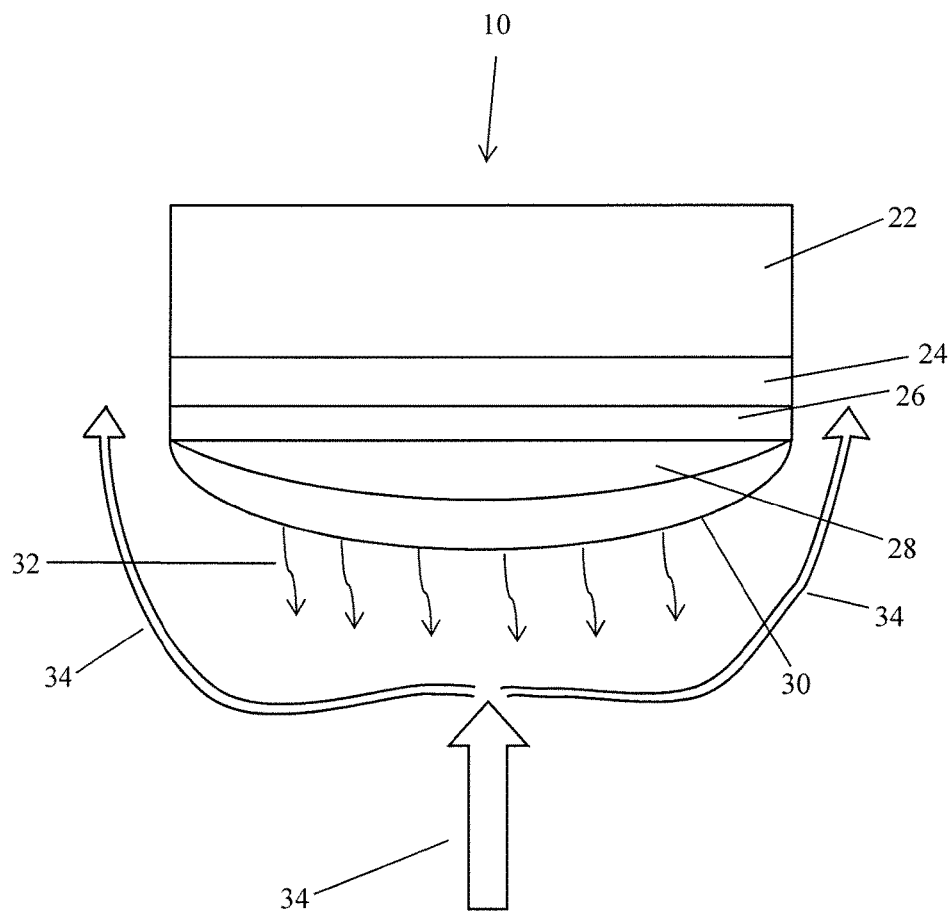
FIG. 5 shows an example of the first embodiment during a puff.

FIG. 5 shows an example of the first embodiment of the subject invention during a puff. FIG. 5 shows the liquid reservoir 22 which is connected via a diffusion medium 24 to the capillary wick disk 26. FIG. 5 shows the mesh heater disk 30 during a puff by the consumer. It can be seen that the deformation of the mesh heater disk 30 upon heating has occurred so that a gap 28 between the capillary wick disk 26 forming the release medium and the mesh heater disk 30 forming the heater has occurred. Since FIG. 5 shows the embodiment during a puff with the mesh heater disk 30 being heated and deformed, the liquid on the mesh heater disk 30 is evaporated as indicated by arrows 32. The airflow in FIG. 5 is from bottom to top and passes on both sides the aerosol-generating device 10, as indicated by hollow arrows 34 in FIG. 5. That means, that the evaporating vapour is taken up by the airflow 34, is cooling down within the airflow to form an aerosol which will be transported to the consumer's mouth.

Figure 6:
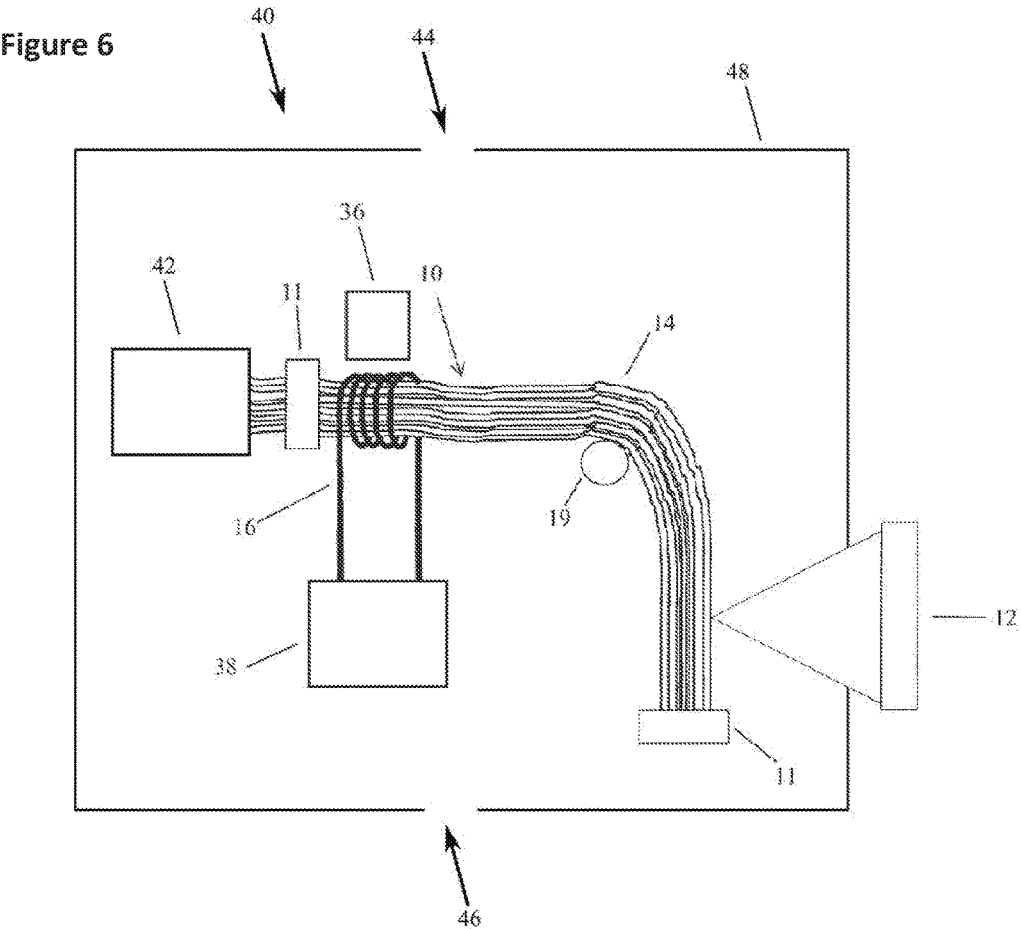
FIG. 6 shows an example of an aerosol-generating system consistent with an embodiment of the invention.

FIG. 6 shows an aerosol-generating system 40 consistent with the disclosed embodiments of the invention. The aerosol-generating system 40 comprises an aerosol-generating device 10 as described earlier with reference to FIG. 1 and comprising a reservoir 42 to hold a liquid. The aerosol-generating system 40 comprises energy source 38 that is connected to the coiled wire 16 and either to the button 12 or to an air flow sensor 36. The aerosol-generating system 40 comprises an air inlet 44 and an sir outlet 46 in housing 48 defining an air flow route from the air inlet 44 via the coiled wire 16 to the air outlet 46 so as to convey an aerosol formed at the coiled sire 16 to the air outlet 46.

The invention claimed is:

1. An aerosol-generating device, comprising:
   a reservoir configured to hold a liquid;
   a release medium; and
   a heater,
   wherein the reservoir and the release medium are configured to transport liquid from the reservoir to the release medium,
   wherein the release medium and the heater are reversibly connected with each other among a first position in which the release medium is in physical contact with the heater and a second position in which a gap separates the release medium and the heater,
   wherein the aerosol-generating device further comprises a means for reversibly connecting the release medium and the heater among the first position and the second position, and
   wherein the aerosol-generating device is configured to activate the heater in the second position when the gap separates the heater and the release medium.

2. The aerosol-generating device according to claim 1, wherein the means for reversibly connecting the release medium and the heater is activated and deactivated automatically during use of the aerosol-generating device.

3. The aerosol-generating device according to claim 1, wherein the means for reversibly connecting the release medium and the heater is switched on and off by a releasing means.

4. The aerosol-generating device according to claim 3, wherein the releasing means is a button.

5. The aerosol-generating device according to claim 2, wherein the heater is also the means for reversibly connecting the release medium and the heater, and is a mesh heater disk comprising at least two different materials, which upon heating lead to different deformations that result in an interruption of the physical contact in the first position and to the formation of the gap that separates the mesh heater disk and the release medium in the second position.

6. The aerosol-generating device according to claim 2, wherein the heater is also the means for reversibly connecting the release medium and the heater, and is a mesh heater disk with a ring surrounding the mesh heater disk,
   wherein the mesh heater disk and the surrounding ring are made from different materials, and
   wherein the surrounding ring is deformable upon heating, which deformation results in an interruption of the physical contact in the first position and to the formation of the gap that separates the mesh heater disk and the release medium in the second position.

7. The aerosol-generating device according to claim 3, wherein the release medium is a capillary wick and the heater is a coil of wire that at least partially surrounds the capillary wick.

8. The aerosol-generating device according to claim 7, wherein the capillary wick is stretched such that a length thereof is increased and a diameter thereof is decreased.

9. The aerosol-generating device according to claim 8, wherein the means for reversibly connecting the release medium and the heater is a button, which, when pressed, contacts with and stretches the capillary wick.

10. The aerosol-generating device according to claim 8, wherein the means for reversibly connecting the release medium and the heater is a button, which is connected to the capillary wick and, when pressed, stretches the capillary wick by a pulling along an axis perpendicular to a longitudinal axis of the capillary wick.

11. The aerosol-generating device according to claim 7, wherein the capillary wick is twisted such that a diameter thereof is decreased.

12. The aerosol-generating device according to claim 11, wherein the means for reversibly connecting the release medium and the heater is a button that is connected to the capillary wick and, when pressed, leads to a rotation along a longitudinal axis of the capillary wick, which rotation leads to twisting of the capillary wick.

13. The aerosol-generating device according to claim 4, wherein the heater is a mesh heater disk with a deformable ring surrounding the mesh heater disk and the means for reversibly connecting the release medium and the heater is the button, and
   wherein upon pressing the button the deformable ring is deformed, which in turn leads to an interruption of the physical contact in the first position and to the formation of the gap that separates the mesh heater disk and the release medium in the second position.

14. The aerosol-generating device according to claim 2, wherein the means for reversibly connecting the release medium and the heater is a magnet and the heater is a magnetically activated mesh heater disk, and
   wherein upon switching on the magnet, a magnetic field is applied that causes deformation of the magnetically activated mesh heater disk, which in turn leads to an interruption of the physical contact in the first position and to the formation of the gap that separates the magnetically activated mesh heater disk and the release medium in the second position.

15. An aerosol-generating system, comprising:
   an aerosol-generating device, comprising a reservoir configured to hold a liquid, a release medium, and a heater, wherein the reservoir and the release medium are configured to transport liquid from the reservoir to the release medium, wherein the release medium and the heater are reversibly connected with each other among a first position in which the release medium is in physical contact with the heater and a second position in which a gap separates the release medium and the heater, wherein the aerosol-generating device further comprises a means for reversibly connecting the release medium and the heater among the first position and the second position, and wherein the aerosol-generating device is configured to activate the heater in the second position when the gap separates the heater and the release medium;

an energy source that is connected to the heater and either to the releasing means or to an air flow sensor; and at least one air inlet and at least one air outlet defining an air flow route from the at least one air inlet via the heater to the at least one air outlet so as to convey an aerosol formed at the heater to the at least one air outlet.

16. A method for heating liquid in an aerosol-generating device comprising a reservoir containing a liquid, a release medium, and a heater, the reservoir being configured to deliver the liquid from the reservoir to the release medium, the method comprising:

arranging the release medium and the heater in a first position in which the release medium is in physical contact with the heater, such that the liquid is transported from the release medium to the heater;

moving the release medium or the heater, or moving both the release medium and the heater, to a second position in which a gap separates the heater and the release medium;

heating the heater while the heater and the release medium are in the second position; and after the heating, returning the release medium and the heater to the first position.

17. The method according to claim 16, further comprising turning off the heater when the release medium and the heater are in the first position.

* * * * *